United States Patent
Gschneidner

(10) Patent No.: US 7,417,061 B2
(45) Date of Patent: *Aug. 26, 2008

(54) OXADIAZOLE COMPOUNDS AND COMPOSITIONS FOR DELIVERING ACTIVE AGENTS

(75) Inventor: David Gschneidner, Thornwood, NY (US)

(73) Assignee: MHR Institutional Partners IIA LP, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/440,332

(22) Filed: May 23, 2006

(65) Prior Publication Data

US 2006/0210533 A1  Sep. 21, 2006

Related U.S. Application Data

(63) Continuation of application No. 09/913,049, filed as application No. PCT/US00/03899 on Feb. 11, 2000, now Pat. No. 7,084,279.

(60) Provisional application No. 60/119,638, filed on Feb. 11, 1999.

(51) Int. Cl.
*A61K 31/41* (2006.01)
*C07D 271/10* (2006.01)

(52) U.S. Cl. ........................ 514/364; 548/143

(58) Field of Classification Search ............. 548/143; 514/364

See application file for complete search history.

(56) References Cited

U.S. PATENT DOCUMENTS 2,765,304 A 10/1956 Siegrist et al.
3,964,896 A 6/1976 Brouwer et al.
5,583,020 A 12/1996 Sullivan
7,084,279 B1 * 8/2006 Gschneidner ............... 548/143

FOREIGN PATENT DOCUMENTS

| DE | 2651386 | 5/1978 |
| EP | 0608858 | 8/1994 |
| JP | 42020057 | 10/1967 |
| WO | WO 03/072195 | * 9/2003 |

OTHER PUBLICATIONS

Obach R. S., Drug-drug interactions: An important negative attribute in drugs, Drugs of Today, 39(5), 301-38, (2003).*
Mehta, et al. "Studies on Ureas. Part-I. Preparation and Antimicrobial Activity of N1-Aryl-N3-2-p-chlorophenyl-1,3,4-oxadiazol-5-ylacylureas." Journal of the Indian Chemical Society, 1988, vol. LXV, No. 7, pp. 521-522.
Raap, "Some Syntheses with Dimehtyl Momothionemalonate." Canadian Journal of Chemistry, 1968, vol. 46, pp. 2255-2261.
Maillard, et al. "Anti-inflammatoires Dérivés de l'acide Phénylacétique; Dérivés Substitués par un Hétérocycle sur le Noyau Phényle." Chimie Therapeutique, 1973, vol. VIII, No. 4, pp. 487-494.
Takahashi, et al. "The Synthesis of 1,3,4-Oxadiazolo[3,2-b]isoquinoline and 1,3,4-Thiadiazaolo-[3,2-b]isoquinoline Derivatives from Homophthalic Anhydride." Bulletin of the Chemical Society of Japan, 1975, vol. 48, No. 10, pp. 2915-2917.
Micetich, et al. "Antibacterial Activity of 6-(5-Membered heteroarylacetamido)penicillanic Acids." Journal of Medicinal Chemistry, 1972, vol. 15, No. 3, pp. 333-335.
Short, et al. "Synethesis of 5-Aryl-2-oxazolepropionic Acids and Analogs. Antiinflammatory Agents." Journal of Heterocyclic Chemistry, 1969, vol. 6, No. 5, pp. 707-712.

* cited by examiner

*Primary Examiner*—Rebecca L Anderson
(74) *Attorney, Agent, or Firm*—Darby & Darby, P.C.

(57) ABSTRACT

Oxadiazole compounds and compositions for the delivery of active agents are provided. Methods of administration and preparation are provided as well.

18 Claims, No Drawings

US 7,417,061 B2

OXADIAZOLE COMPOUNDS AND COMPOSITIONS FOR DELIVERING ACTIVE AGENTS

This application is a continuation of U.S. Ser. No. 09/913,049 filed Sep. 12, 2001, which is the National Stage of PCT/US00/03899 filed Feb. 11, 2000, which claims the benefit of U.S. Provisional Ser. No. 60/119,638, filed Feb. 11, 1999. Each of the above applications are hereby incorporated by reference in their entirety.

FIELD OF THE INVENTION

The present invention relates to oxadiazole compounds for delivering active agents, such as biologically or chemically active agents, to a target. These compounds are well suited for forming non-covalent mixtures with active agents for oral, intracolonic, or other routes of administration to animals. Methods for the preparation and administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents may be rapidly rendered ineffective or destroyed in the gastrointestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, proteinoid microspheres have been used to deliver pharmaceuticals. For example, see U.S. Pat. No. 5,401,516, U.S. Pat. No. 5,443,841 and U.S. RE35,862. In addition, certain modified amino acids have been used to deliver pharmaceuticals. See, e.g., U.S. Pat. No. 5,629,020; U.S. Pat. No. 5,643,957; U.S. Pat. No. 5,766,633; U.S. Pat. No. 5,776,888; and U.S. Pat. No. 5,866,536.

However, there is still a need for simple, inexpensive delivery systems which are easily prepared and which can deliver a broad range of active agents by various routes.

SUMMARY OF THE INVENTION

Compounds and compositions that are useful in the delivery of active agents are provided. The present invention encompasses compounds having the following formula, salts thereof, polymorphs thereof, or mixtures thereof.

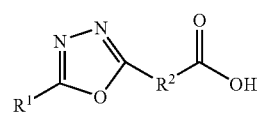

Formula I wherein
$R^1$ is $C_1$-$C_{10}$ alkyl, $C_2$-$C_{10}$ alkenyl, $C_2$-$C_{10}$ alkynyl, $C_3$-$C_{10}$ cycloalkyl, phenyl, naphthyl, or aromatic heterocycle;

$R^1$ is optionally substituted with $C_1$-$C_4$ alkyl or fluoroalkyl, $C_2$-$C_4$ alkenyl, $C_1$-$C_4$ alkoxy or fluoroalkoxy, halogens, —OH, —SH, phenyl, phenoxy, —$CO_2R_3$, —$N(CH_3)_2$, —$NO_2$, or —$NH_2$.

$R^2$ is $C_1$-$C_{24}$ alkylene, $C_2$-$C_{24}$ alkenylene, $C_3$-$C_{10}$ cycloalkylene, $C_3$-$C_{10}$ cycloalkenylene, phenylene, naphthylene, ($C_1$-$C_{10}$ alkyl)phenylene, ($C_2$-$C_{10}$ alkenyl)phenylene, ($C_1$-$C_{10}$ alkyl)naphthylene, ($C_2$-$C_{10}$ alkenyl)naphthylene, phenyl($C_1$-$C_{10}$ alkylene), phenyl($C_2$-$C_{10}$ alkenylene), naphthyl($C_1$-$C_{10}$ alkylene) or naphthyl($C_2$-$C_{10}$ alkenylene);

$R^2$ is optionally substituted with $C_1$-$C_4$ alkyl or fluoroalkyl, $C_2$-$C_4$ alkenyl, $C_1$-$C_4$ alkoxy or fluoroalkoxy, halogens, —OH, —SH, phenyl, phenoxy, —$CO_2R_3$, —$N(CH_3)_2$, —$NO_2$, —$NH_2$, $C_3$-$C_{10}$ cycloalkyl, $C_3$-$C_{10}$ cycloalkenyl, aryl, ($C_1$-$C_{10}$ alk)aryl, heterocycle having 3-10 ring atoms wherein the hetero atom is one or more of N, O, S or any combination thereof, or any combination thereof;

$R^2$ being optionally interrupted by oxygen, nitrogen, sulfur, or any combination thereof; and $R^3$ is hydrogen, $C_1$-$C_4$ alkyl, or $C_2$-$C_4$ alkenyl, with the provisos that $R^1$ is not 4-(piperidin-4-yl)phenyl when $R^2$ is —$(CH_2)_4$—; $R^1$ is not —$CH_3$ when $R^2$ is —$(CH_2)_3$—; $R^1$ is not 4-cycloalkyl, when $R^2$ is —$(CH_2)_3$—or —$(CH_2)_4$—.

Preferably, $R^1$ is $C_1$-$C_6$ alkyl, $C_2$-$C_6$ alkenyl, $C_2$-$C_6$ alkynyl, cycloalkyl, phenyl, or naphthyl and $R^1$ is optionally substituted with halogens, —OH, —SH, $C_1$-$C_4$ alkyl or $C_1$-$C_4$ alkoxy. More preferably, $R^1$ is a substituted or unsubstituted phenyl or naphthyl, —$CH_3$, or —$CH_2OH$. Most preferably, $R^1$ is 2-OH-phenyl, optionally further substituted with —OH, Cl, —$CH_3$ or —$OCH_3$.

Preferably, $R^2$ is $C_1$-$C_{24}$ alkylene or ($C_1$-$C_{10}$ alkyl)phenylene. More preferably, $R^2$ is $C_4$-$C_8$ alkylene.

More preferred compounds include, but are not limited to, those having the formulas:

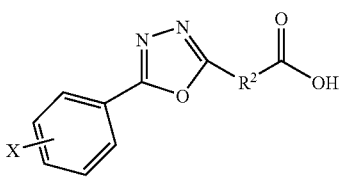

wherein

| Cpd # | X | R² |
|---|---|---|
| 1 | 2-OH | $(CH_2)_8$ |
| 2 | 2-OH | $(CH_2)_6$ |
| 3 | 2-OH | $(CH_2)_4$ |
| 4 | 2-OH | $(CH_2)_7$ |
| 5 | 2-OH-5-Cl | $(CH_2)_6$ |
| 6 | 2-OH-3,5-di-Cl | $(CH_2)_6$ |
| 7 | 2-OH-4-methyl | $(CH_2)_6$ |
| 8 | 2-OH-4-OMe | $(CH_2)_6$ |
| 9 | 2-OH-4-OMe | $(CH_2)_4$ |
| 10 | H | $(CH_2)_6$ |
| 11 | 2-Cl | $(CH_2)_6$ |

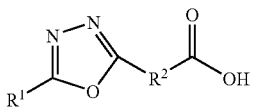

wherein

| Cpd# | R¹ | R² |
|---|---|---|
| 12 | $CH_3$ | $(CH_2)_6$ |
| 13 | $CH_2OH$ | $(CH_2)_6$ | polymorphs thereof, and salts thereof.

These compounds may be referred to as oxadiazoles.

The compositions of the present invention comprise at least one active agent, preferably a biologically or chemically active agent, and at least one of the compounds or salts thereof of the present invention of the structure of Formula I above, including all the particular embodiments referred to above as well as those excluded by proviso, and also including compounds 1-13. These compounds may have the formula

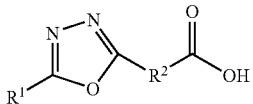

wherein $R^1$ is $C_1$-$C_{10}$ alkyl, $C_2$-$C_{10}$ alkenyl, $C_2$-$C_{10}$ alkynyl, $C_3$-$C_{10}$ cycloalkyl, phenyl, naphthyl, or aromatic heterocycle;

$R^1$ is optionally substituted with $C_1$-$C_4$ alkyl or fluoroalkyl, $C_2$-$C_4$ alkenyl, $C_1$-$C_4$ alkoxy or fluoroalkoxy, halogens, —OH, —SH, phenyl, phenoxy, —$CO_2R_3$, —$N(CH_3)_2$, —$NO_2$, or —$NH_2$.

$R^2$ is $C_1$-$C_{24}$ alkylene, $C_2$-$C_{24}$ alkenylene, $C_3$-$C_{10}$ cycloalkylene, $C_3$-$C_{10}$ cycloalkenylene, phenylene, naphthylene, ($C_1$-$C_{10}$ alkyl)phenylene, ($C_2$-$C_{10}$ alkenyl)phenylene, ($C_1$-$C_{10}$ alkyl)naphthylene, ($C_2$-$C_{10}$ alkenyl)naphthylene, phenyl($C_1$-$C_{10}$ alkylene), phenyl($C_2$-$C_{10}$ alkenylene), naphthyl($C_1$-$C_{10}$ alkylene) or naphthyl($C_2$-$C_{10}$ alkenylene);

$R_2$ is optionally substituted with $C_1$-$C_4$ alkyl or fluoroalkyl, $C_2$-$C_4$ alkenyl, $C_1$-$C_4$ alkoxy or fluoroalkoxy, halogens, —OH, —SH, phenyl, phenoxy, —$CO_2R_3$, —$N(CH_3)_2$, —$NO_2$, —$NH_2$, $C_3$-$C_{10}$ cycloalkyl, $C_3$-$C_{10}$ cycloalkenyl, aryl, ($C_1$-$C_{10}$ alk)aryl, heterocycle having 3-10 ring atoms wherein the hetero atom is one or more of N, O, S or any combination thereof, or any combination thereof;

$R^2$ being optionally interrupted by oxygen, nitrogen, sulfur, or any combination thereof; and $R^3$ is hydrogen, $C_1$-$C_4$ alkyl, or $C_2$-$C_4$ alkenyl. Methods for the preparation and administration of such compositions are also provided.

Also provided are dosage unit forms comprising the composition of the present invention. The dosing vehicle can be a solid (such as a tablet, powder, or capsule) or a liquid.

Methods for administering a biologically active agent to an animal in need of the agent, especially by the oral or intracolonic routes, with the compositions of the present invention, are also provided.

DETAILED DESCRIPTION OF THE INVENTION

Compounds

The compounds may be in the form of the carboxylic acid and/or their salts. Salts include but are not limited to organic and inorganic salts, for example alkali-metal salts, such as sodium, potassium and lithium; alkaline-earth metal salts, such as magnesium, calcium or barium; ammonium salts; basic amino acids, such as lysine or arginine; and organic amines, such as dimethylamine or pyridine. Preferably, the salts are sodium salts.

In general, the compounds of the present invention may be prepared by dehydrative cyclization of dihydrazides, protecting any functional groups present in the dihydrazide as necessary. Dehydrative cyclization may be performed by reacting dihydrazide with carbon tetrachloride and triphenylphosphene in the presence of an organic base, such as triethylamine. The acid is formed from basic hydrolysis of the resulting ester. Suitable solvents for the cyclization reaction include, but are not limited to, acetonitrile.

The compound may be purified by recrystallization or by fractionation on one or more solid chromatographic supports, alone or linked in tandem. Suitable recrystallization solvent systems include, but are not limited to, acetonitrile, methanol, and tetrahydrofuran. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

Active Agents

Active agents suitable for use in the present invention include biologically active agents and chemically active agents, including, but not limited to, pesticides, pharmacological agents, and therapeutic agents.

For example, biologically or chemically active agents suitable for use in the present invention include, but are not limited to, proteins; polypeptides; peptides; hormones; polysaccharides, and particularly mixtures of muco-polysaccharides; carbohydrates; lipids; other organic compounds; and particularly compounds which by themselves do not pass (or which pass only a fraction of the administered dose) through the gastro-intestinal mucosa and/or are susceptible to chemical cleavage by acids and enzymes in the gastro-intestinal tract; or any combination thereof.

Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone-releasing hormones; interferons, including $\alpha$, $\beta$ and $\gamma$; interleukin-1; interleukin-2; insulin, including porcine, bovine, human, and human recombinant, optionally having counter ions including sodium, zinc, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); parathyroid hormone (PTH), including its fragments; antimicrobials, including anti-fungal agents; vitamins; analogs, fragments, mimetics or polyethylene glycol (PEG)-modified derivatives of these compounds; or any combination thereof.

Delivery Systems

The compositions of the present invention comprise a delivery agent, i.e., a compound of the present invention, and one or more active agents. In one embodiment, one or more of the delivery agent compounds, or salts of these compounds, may be used as a delivery agent by mixing with the active agent prior to administration.

The administration compositions may be in the form of a liquid. The solution medium may be water (for example, for salmon calicitonin, parathyroid hormone, and erthyropoietin), 25% aqueous propylene glycol (for example, for heparin) and phosphate buffer (for example, for rhGH). Other dosing vehicles include polyethylene glycols, sorbitol, maltitol, and sucrose. Dosing solutions may be prepared by mixing a solution of the delivery agent compound with a solution of the active agent, just prior to administration. Alternately, a solution of the delivery agent (or active agent) may be mixed with the solid form of the active agent (or delivery agent). The delivery agent compound and the active agent may also be mixed as dry powders. The delivery agent compound and the active agent can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or powder. Solid dosage forms may be prepared by mixing the solid form of the compound with the solid form of the active agent. Alternately, a solid may be obtained from a solution of compound and active agent by methods known in the art, such as freeze drying, precipitation, crystallization and solid dispersion.

The administration compositions of the present invention may also include one or more enzyme inhibitors. Such enzyme inhibitors include, but are not limited to, compounds such as actinonin, epiactinonin, and derivatives thereof. Other enzyme inhibitors include, but are not limited to, aprotinin (Trasylol) and Bowman-Birk inhibitor.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of compound/active agent compositions or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the compositions may deliver active agents more efficiently than prior compositions, lower amounts of biologically or chemically active agents than those used in prior dosage unit forms or delivery systems can be administered to the subject, while still achieving the same blood levels and/or therapeutic effects.

The presently disclosed compounds facilitate delivery of biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering biologically or chemically active agents to any animals, including but not limited to birds such as chickens; mammals, such as rodents, cows, pigs, dogs, cats, primates, and particularly humans; and insects.

The present invention is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful in orally administering active agents, especially those that are not ordinarily orally deliverable, or those for which improved delivery is desired.

The compositions comprising the compounds and active agents have utility in the delivery of active agents to selected biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery) or over a period of time (such as sustained delivery).

Following administration, the active agent present in the composition or dosage unit form is taken up into the circulation. The bioavailability of the agent is readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

DESCRIPTION OF THE PREFERRED EMBODIMENTS

The following examples illustrate the invention without limitation. All parts are given by weight unless otherwise indicated.

EXAMPLE 1

Compound 2 was prepared as follows. A suspension of 30.34 g (0.108 mol) of N-(methyl suberoyl)-N'-salicyloylhydrazide and 138 mL of methylene chloride was cooled to 0° C. in an ice bath and treated with 16.56 mL (12.0 g, 0.119 mol) of triethylamine, followed by 14.40 mL (12.3 g, 0.113 mol) of trimethylsilylchloride 15 minutes later. After warming to 25° C. and stirring for 3 hours, the reaction mixture was concentrated in vacuo.

The residue was taken up in 183 mL of acetonitrile and treated with 45.16 mL (32.8 g, 0.324 mol) of triethylamine, 50.4 mL (80.2 g, 0.522 mol) of carbon tetrachloride and 63.88 g (0.243 mol) of triphenylphosphine. The orange slurry was stirred for 18 hours. The solid was removed by filtration. The filtrate was diluted with 183 mL of ethyl acetate, washed with 2% aqueous hydrochloric acid (2×100 mL) dried over sodium sulfate and concentrated in vacuo.

The resulting solid was brought up in 60 mL of 2N aqueous sodium hydroxide and stirred at 65° C. for three hours. The undissolved solid was removed by filtration. The filtrate was acidified to pH 3 with 3% aqueous hydrochloric acid. The resulting solid was isolated by filtration and recrystallized from ethanol/water. A total of 11.76 g, having a melting point of 109-112° C., was collected.

Compounds 1, 3-8, 10 and 12 were also prepared by this method with the appropriate starting materials. Compounds 9, 11 and 13 may also be prepared by this method using the appropriate starting materials.

EXAMPLE 2

Salmon Calcitonin (sCT)

Oral Delivery

Oral dosing (PO) compositions of delivery agent compound and salmon calcitonin (sCT) in water were prepared. Typically, 450 mg of compound was added to 2.0 ml of water. Either the sodium salt of the compound was used or the free acid was converted to the sodium salt by stirring the resultant solution and adding one equivalent of sodium hydroxide (1.0 N) and diluting with water. The solution was vortexed, then heated (about 37° C.) and sonicated. The pH was adjusted to about 7 (6.5 to 8.5) with sodium hydroxide or hydrochloric acid. 90 μg sCT from a stock solution was added to the solution. Water was then added to bring the total volume to about 3.0 ml (varies depending on solubility of the delivery agent compound) and vortexed. The final delivery agent compound dose, sCT dose and volume dose amounts are listed below in Table 1.

The typical dosing and sampling protocols were as follows. Male Sprague-Dawley rats weighing between 200-250 g were fasted for 24 hours and administered ketamine (44 mg/kg) and chlorpromazine (1.5 mg/kg) 15 minutes prior to dosing. A dosing group of five rats was administered one of the dosing solutions. For oral dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. Solution was administered by pressing the syringe plunger.

Blood samples were collected serially from the tail artery, typically at 0, 10, 20, 30, 60 and 90 minutes after administration. Serum sCT was determined by testing with an EIA kit (Kit # EIAS-6003 from Peninsula Laboratories, Inc., San Carlos, Calif.). Numbers were adjusted according to baseline values obtained at 0 minutes. The limit of the assay is 80 pg/ml. The results from the five rats in each dosing group were averaged for each time point. The maximum is reported below in Table 1.

TABLE 1

Oral Delivery of Salmon Calcitonin (sCT)

| Compound | Volume Dose (ml/kg) | Compound Dose (mg/kg) | sCT Dose (μg/kg) | Mean Peak Serum Sct (pg/ml ± SD)(SE) |
|---|---|---|---|---|
| 1 | 1 | 150 | 30 | 167 ± 89 (39) |
| 2 | 1 | 150 | 30 | 260 ± 146 (65) |
| 2 | 1 | 150 | 30 | 112 ± 69 (31) |
| 2 | 1 | 150 | 30 | 165 ± 136 (61) |
| 2 | 1 | 150 | 30 | 160 ± 207 (93) |
| 2 | 1 | 150 | 30 | 492 ± 830 (10) |
| *3 | 1 | 150 | 30 | 271 ± 503 (225) |
| 3 | 1 | 150 | 30 | 444 ± 277 (124) |
| 3 | 1 | 150 | 30 | 108 ± 115 (52) |
| 4 | 1 | 150 | 30 | 272 ± 284 (127) |
| 4 | 1 | 150 | 30 | 253 ± 374 (167) |
| 5 | 1 | 150 | 30 | 393 ± 431 (193) |
| 6 | 1 | 150 | 30 | 306 ± 339 (152) |
| 8 | 1 | 150 | 30 | 168 ± 217 (97) |
| 8 | 1 | 150 | 30 | 204 ± 227 (102) |
| 10 | 1 | 150 | 30 | 37 ± 55 |
| 12 | 1 | 150 | 30 | 212 ± 194 (433) |
| 12 | 1 | 150 | 30 | 155 ± 134 (60) |

*In this dosing of compound 3, the standard protocol was modified from the kit as follows: incubated with 50 μl peptide antibody for 2 hours with shaking in the dark, washed the plate, added serum and biotinylated peptide and diluted with 4 ml buffer, and shook overnight in the dark.

EXAMPLE 3

Heparin Delivery

Oral/Intracolonic Delivery

Oral gavage (PO) and/or intracolonic (IC) dosing solutions containing a delivery agent compound and heparin sodium USP in 25% aqueous propylene glycol were prepared. Either the sodium salt of the compound was used or the free acid was converted to the sodium salt with one equivalent of sodium hydroxide. Typically, delivery agent compound and heparin (about 166-182 IU/mg) were mixed by vortex as dry powders. This dry mixture was dissolved in 25% v/v aqueous propylene glycol, vortexed and placed in a sonicator (about 37° C.). The pH was adjusted to about 7 (6.5 to 8.5) with aqueous sodium hydroxide (2N). The dosing solution was sonicated to produce a clear solution. The final volume was adjusted to about 3.0 ml. The final delivery agent compound dose, heparin dose and volume dose amounts are listed below in Table 2.

The typical dosing and sampling protocols were as follows. Male Sprague-Dawley rats weighing between 275-350 g were fasted for 24 hours and were anesthetized with ketamine hydrochloride (88 mg/kg) intramuscularly immediately prior to dosing. A dosing group of five rats was administered one of the dosing solutions. For oral gavage (PO) dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the rat's incisors. Solution was administered by pressing the syringe plunger. For intracolonic (IC) dosing, a 7.5cm, 8 fr Rusch catheter was adapted to a 1 ml syringe with a pipette tip. The dosing catheter was inserted into the colon through the anus until the tube was no longer visible. The dosing solution was expressed slowly into the colon by pressing the syringe plunger.

Citrated blood samples were collected by cardiac puncture following the administration of ketamine (88 mg/kg), typically at 0.25, 0.5, 1.0 and 1.5 hours after administration. Heparin activity was determined by utilizing the activated partial thromboplastin time (APTT) according to the method of Henry, J. B., Clinical Diagnosis and Management by Laboratory Methods, Philadelphia, Pa., W. B. Saunders (1979). Previous studies indicated baseline values of about 20 sec. Results from the five rats in each group were averaged for each time point. The maximum is reported below in Table 2.

TABLE 2

Oral/Intracolonic Delivery of Heparin

| Compound | Method of Administration | Volume dose (ml/kg) | Compound Dose (mg/kg) | Heparin Dose (mg/kg) | Mean Peak APTT (sec) ± SD |
|---|---|---|---|---|---|
| 1 | IC | 1 | 50 | 25 | 38.4 ± 17.4 |
| 2 | IC | 1 | 50 | 25 | 52.8 ± 31.9 |

EXAMPLE 4

Recombinant Human Growth Hormone (rhGH)

Oral/Intracolonic Delivery

Oral gavage (PO) and/or intracolonic (IC) dosing solutions of delivery agent compound and rhGH in phosphate buffer were prepared. A solution of the compound was made either with the sodium salt of the compound or by converting the free acid to its sodium salt. Typically, a solution of the compound was prepared in phosphate buffer and stirred, adding one equivalent of sodium hydroxide (1.0 N) when making the sodium salt. The final dosing solutions were prepared by mixing the compound solution with an rhGH stock solution (15 mg rhGH/ml) and diluting to the desired volume (usually 3.0 ml). The compounds and rhGH dose amounts are listed below in Table 3.

The typical dosing and sampling protocols were as follows. Male Sprague-Dawley rats weighing between 200-250 g were fasted for 24 hours and administered ketamine (44 mg/kg) and chlorpromazine (1.5 mg/kg) 15 minutes prior to dosing. A dosing group of five rats was administered one of the dosing solutions. For oral gavage (PO), an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the rat's incisors. Solution was administered by pressing the syringe plunger. For intracolonic (IC) dosing, a 7.5 cm Rusch catheter tube (French 8 or 6) was adapted to a syringe with an Eppendorf pipette tip. The syringe was filled with the dosing solution by drawing the solution through the catheter tube. The catheter tube was wiped dry. K-Y jelly was applied to the tip, avoiding contact with the eye of the tube, and the tube was inserted into the colon through the anus until the tube was no longer visible. The solution was injected by pressing the syringe plunger, and the tube was removed.

Blood samples were collected serially from the tail artery, typically at 0, 15, 30, 45, 60 and 90 minutes after oral administration and 0, 10, 20, 30, 60 and 90 minutes after IC administration. The five samples from each time period were pooled (except for where compound 1 was dosed). Serum rHGH concentrations were quantified by an rHGH immunoassay test kit (Kit # K1F4015 from Genzyme Corporation Inc., Cambridge, Mass.). Previous studies indicated baseline values of about zero.

The maximum concentration for each group and the area under the curve (AUC), when available, are reported below in Table 3.

TABLE 3

Oral/Intracolonic Delivery of rhGH in Rats

| Compound | Method of Administration | Volume dose (ml/kg) | Compound Dose (mg/kg) | rhGH Dose (mg/kg) | Mean Peak Serum [rhGH] (ng/ml) | AUC |
|---|---|---|---|---|---|---|
| 1 | PO | 1 | 200 | 3 | 4.42 ± 4.42 | 142.25 |
| 1 | PO | 1 | 200 | 3 | 11.1 ± 8.9 | 218.7 |
| 2 | PO | 1 | 200 | 3 | 3.77 | 56.55 |
| 3 | PO | 1 | 200 | 3 | 88.9 | 133.5 |
| 3 | PO | 1 | 200 | 3 | 35.08 | 969.6 |
| 5 | PO | 1 | 200 | 3 | 14.64 | 219.6 |
| 6 | PO | 1 | 200 | 3 | 0 | 0 |
| 7 | PO | 1 | 200 | 3 | 0.045 | 60 |
| 8 | PO | 1 | 200 | 3 | 9.81 | 2187.7 |
| 8 | PO | 1 | 200 | 3 | 0 | 0 |
| 9 | PO | 1 | 200 | 3 | 14.25 | |
| 10 | PO | 1 | 200 | 3 | 14.25 | 802.725 |
| 12 | PO | 1 | 200 | 3 | 0 | 0 |

EXAMPLE 5

Parathyroid Hormone Delivery (PTH 1-34)

Oral/Intracolonic Delivery

Oral gavage (PO) and/or intracolonic (IC) dosing solutions of delivery agent compound and human parathyroid hormone residues 1-34 (PTH) in water were prepared. A solution of the compound was made either with the sodium salt of the compound or by converting the free acid to its sodium salt. Typically, a solution of the compound was prepared in water and stirred, adding one equivalent of sodium hydroxide (1.0 N) when making the sodium salt. The final dosing solutions were prepared by mixing the compound solution with a PTH stock solution (typically having a concentration of 5 mg PTH/ml) and diluting to the desired volume (usually 3.0 ml). The final compound, PTH and volume dose amounts are listed below in Table 4.

The typical dosing and sampling protocols were as follows. Male Sprague-Dawley rats weighing between 200-250 g were fasted for 24 hours and administered ketamine (44 mg/kg) and chlorpromazine (1.5 mg/kg) 15 minutes prior to dosing. A dosing group of five rats was administered one of the dosing solutions. For oral gavage (PO), an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the rat's incisors. Solution was administered by pressing the syringe plunger. For intracolonic (IC) dosing, a 7.5 cm Rusch catheter tube (French 8 or 6) was adapted to a syringe with an Eppendorf pipette tip. The syringe was filled with the dosing solution by drawing the solution through the catheter tube. The catheter tube was wiped dry. K-Y jelly was applied to the tip, avoiding contact with the eye of the tube, and the tube was inserted into the colon through the anus until the tube was no longer visible. The solution was injected by pressing the syringe plunger, and the tube was removed.

Blood samples were collected serially from the tail artery, typically 0, 15, 30, 45, 60 and 90 minutes after oral administration and 0, 10, 20, 30, 60 and 90 minutes after IC administration. Serum PTH concentrations were quantified by a PTH radioimmunoassay kit (Kit # RIK 6101 from Peninsula Laboratories, Inc., San Carlos, Calif.). Previous studies indicated baseline values of about zero. Results from the five rats in each group were averaged for each time point. The maximum is reported below in Table 4.

Many variations of the present invention will suggest themselves to those skilled in the art in light of the above detailed description. All such obvious variations are within the fully intended scope of the appended claims

What is claimed is:

1. A pharmaceutical composition comprising:
(A) an active agent; and
(B) at least one compound selected from:

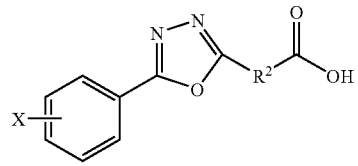

| Cpd # | X | $R^2$ |
|---|---|---|
| 1 | 2-OH | $(CH_2)_8$ |
| 2 | 2-OH | $(CH_2)_6$ |
| 3 | 2-OH | $(CH_2)_4$ |
| 4 | 2-OH | $(CH_2)_7$ |
| 5 | 2-OH-5-Cl | $(CH_2)_6$ |
| 6 | 2-OH-3,5-di-Cl | $(CH_2)_6$ |
| 7 | 2-OH-4-methyl | $(CH_2)_6$ |
| 8 | 2-OH-4-OMe | $(CH_2)_6$ |
| 9 | 2-OH-4-OMe | $(CH_2)_4$ | and salts thereof.

2. The composition of claim 1, wherein the active agent is selected from the group consisting of a biologically active agent, a chemically active agent, and a combination thereof.

3. The composition of claim 2, wherein the biologically active agent comprises at least one protein, polypeptide, peptide, hormone, polysaccharide, mucopolysaccharide, carbohydrate, or lipid.

4. The composition of claim 2, wherein the biologically active agent is selected from the group consisting of growth hormones, human growth hormones (hGH), recombinant human growth hormones (rhGH), bovine growth hormones, porcine growth hormones, growth hormone-releasing hormones, interferons, α-interferon, β-interferon, γ-interferon, interleukin-1, interleukin-2, insulin, porcine insulin, bovine insulin, human insulin, human recombinant insulin, insulin-like growth factor (IGF), IGF-1, heparin, unfractionated heparin, heparinoids, dermatans, chondroitins, low molecular weight heparin, very low molecular weight heparin, ultra low

TABLE 4

Oral/Intracolonic Delivery of PTH in Rats

| Compound | Method of Administration | Volume dose (ml/kg) | Compound Dose (mg/kg) | PTH Dose (µg/kg) | Mean Peak Serum [PTH] (pg/ml) ± SD | AUC |
|---|---|---|---|---|---|---|
| 2 | PO | 1 | 100 | 200 | 498.55 ± 237.83 | |
| 3 | PO | 1 | 100 | 200 | 57.88 ± | 2717.51 |
| 4 | PO | 1 | 100 | 200 | 330.74 ± 410.57 | 6852.12 |
| 5 | PO | 1 | 100 | 200 | 22.91 ± | 509.20 |
| 6 | PO | 1 | 100 | 200 | 14.44 ± | 716.46 |
| 7 | PO | 1 | 100 | 200 | 138.9 ± 118.46 | 4790.10 |

The above mentioned patents, applications, test methods, and publications are hereby incorporated by reference in their entirety.

molecular weight heparin, calcitonin, salmon calcitonin, eel calcitonin, human calcitonin; erythropoietin(EPO), artrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, cyclosporin, vasopressin, cromolyn sodium, sodium chromoglycate, disodium chromoglycate, vancomycin, desferrioxamine (DFO), parathyroid hormone (PTH), fragments of PTH, antimicrobials, anti-fungal agents, vitamins; analogs, fragments, mimetics and polyethylene glycol (PEG)-modified derivatives of these compounds; and any combination thereof.

5. The composition of claim 2, wherein the biologically active agent comprises insulin, unfractionated heparin, low molecular weight heparin, very low molecular weight heparin, ultra low molecular weight heparin, calcitonin, PTH, EPO, hGH or combinations thereof.

6. The composition of claim 2, wherein the biologically active agent comprises salmon calcitonin.

7. The composition of claim 1, wherein the compound is

| Cpd # | X | $R^2$ |
|---|---|---|
| 3 | 2-OH | $(CH_2)_4$ | or a salt thereof.

8. A dosage unit form comprising:
(A) the composition of claim 1; and
(B) (a) an excipient,
   (b) a diluent,
   (c) a disintegrant,
   (d) a lubricant,
   (e) a plasticizer,
   (f) a colorant,
   (g) a dosing vehicle, or
   (h) any combination thereof.

9. The dosage unit form of claim 8, wherein the biologically active agent comprises at least one protein, polypeptide, peptide, hormone, polysaccharide, mucopolysaccharide, carbohydrate, or lipid.

10. The dosage unit form of claim 8, wherein the biologically active agent is selected from the group consisting of growth hormones, human growth hormones (hGH), recombinant human growth hormones (rhGH), bovine growth hormones, porcine growth hormones, growth hormone-releasing hormones, interferons, α-interferon, β-interferon, γ-interferon, interleukin-1, interleukin-2, insulin, porcine insulin, bovine insulin, human insulin, human recombinant insulin, insulin-like growth factor (IGF), IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin; erythropoietin (EPO), atrial naturetic factor, antigens, monoclonal antibodies, somatostatin, protease inhibitors, andrenocorticotropin, gonadotropin releasing hormone, follicle stimulating hormone, glucocerebrosidase, thrombopoietin, filgrastim, prostaglandins, cyclosporin, vasopressin, cromolyn sodium, sodium chromoglycate, disodium chromoglycate, vancomycin, desferrioxamine (DFO), parathyroid hormone (PTH), fragments of PTH, antimicrobials, anti-fungal agents, vitamins; analogs, fragments, mimetics and polyethylene glycol (PEG)-modified derivatives of these compounds; and any combination thereof.

11. The dosage form of claim 9, wherein the biologically active agent comprises insulin, unfractionated heparin, low molecular weight heparin, very low molecular weight heparin, ultra low molecular weight heparin, calcitonin, PTH, EPO, hGH, or combinations thereof.

12. The dosage unit form of claim 8, wherein the active agent comprises salmon calcitonin.

13. The dosage unit form of claim 8, wherein the dosage unit form is in the form of a tablet, a capsule, a powder, or a liquid.

14. A method for preparing a composition comprising mixing:
(A) at least one active agent;
(B) at least one compound selected from:

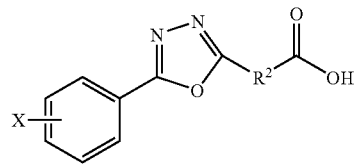

| Cpd # | $R^1$ | $R^2$ |
|---|---|---|
| 1 | 2-OH | $(CH_2)_8$ |
| 2 | 2-OH | $(CH_2)_6$ |
| 3 | 2-OH | $(CH_2)_4$ |
| 4 | 2-OH | $(CH_2)_7$ |
| 5 | 2-OH-5-Cl | $(CH_2)_6$ |
| 6 | 2-OH-3,5-di-Cl | $(CH_2)_6$ |
| 7 | 2-OH-4-methyl | $(CH_2)_6$ |
| 8 | 2-OH-4-OMe | $(CH_2)_6$ |
| 9 | 2-OH-4-OMe | $(CH_2)_4$; and |

(C) optionally, a dosing vehicle.

15. A compound having the formula

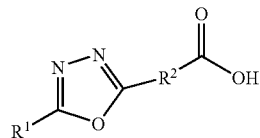

or a salt thereof, wherein
$R^1$ is phenyl substituted with —OH;
$R^1$ is optionally further substituted with one or more of $C_1$-$C_4$ alkyl or fluoroalkyl, $C_2$-$C_4$ alkenyl, $C_1$-$C_4$ fluoroalkoxy, —OH, —SH, phenyl, phenoxy, —$CO_2R^3$, or —$N(CH_3)_2$;
$R^2$ is $C_1$-$C_{24}$ alkylene;
$R^2$ is optionally substituted with one or more of $C_1$-$C_4$ alkyl or fluoroalkyl, $C_2$-$C_4$ alkenyl, $C_1$-$C_4$ alkoxy or fluoroalkoxy, halogens, —OH, —SH, phenyl, phenoxy, —$CO_2R^3$, —$N(CH_3)_2$, —$NO_2$, —$NH_2$, $C_3$-$C_{10}$ cycloalkyl, $C_3$-$C_{10}$ cycloalkenyl, aryl, or ($C_1$-$C_{10}$ alkyl) aryl; and
$R^3$ is $C_1$-$C_4$ alkyl or $C_2$-$C_4$ alkenyl.

16. A pharmaceutical composition comprising:
(A) an active agent; and
(B) a compound having the formula

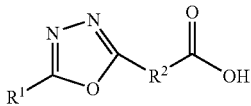

wherein
- $R^1$ is phenyl substituted with —OH;
- $R^1$ is optionally substituted with $C_1$-$C_4$ alkyl or fluoroalkyl, $C_2$-$C_4$ alkenyl, $C_1$-$C_4$ alkoxy or fluoroalkoxy, halogens, —OH, —SH, phenyl, phenoxy, —$CO_2R^3$, —$N(CH_3)_2$, —$NO_2$, or —$NH_2$;
- $R^2$ is $C_1$-$C_{24}$ alkylene;
- $R^2$ is optionally substituted with $C_1$-$C_4$ alkyl or fluoroalkyl, $C_2$-$C_4$ alkenyl, $C_1$-$C_4$ alkoxy or fluoroalkoxy, halogens, —OH, —SH, phenyl, phenoxy, —$CO_2R^3$, —$N(CH_3)_2$, —$NO_2$, $C_3$-$C_{10}$ cycloalkyl, $C_3$-$C_{10}$ cycloalkenyl, aryl, or ($C_1$-$C_{10}$ alkyl)aryl; and
- $R^3$ is hydrogen, $C_1$-$C_4$ alkyl, or $C_2$-$C_4$ alkenyl.

17. A compound having the formula

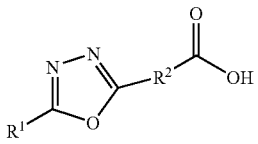

or a salt thereof, wherein
- $R^1$ is phenyl substituted with —OH;
- $R^1$ is optionally further substituted with one or more of $C_1$-$C_4$ alkyl or fluoroalkyl, $C_2$-$C_4$ alkenyl, $C_1$-$C_4$ fluoroalkoxy, halogen, —OH, —SH, phenyl, phenoxy, —$CO_2R^3$, or —$N(CH_3)_2$;
- $R^2$ is $C_4$-$C_8$ alkylene;
- $R^2$ is optionally substituted with one or more of $C_1$-$C_4$ alkyl or fluoroalkyl, $C_2$-$C_4$ alkenyl, $C_1$-$C_4$ alkoxy or fluoroalkoxy, halogens, —OH, —SH, phenyl, phenoxy, —$CO_2R^3$, —$N(CH_3)_2$, —$NO_2$, —$NH_2$, $C_3$-$C_{10}$ cycloalkyl, $C_3$-$C_{10}$ cycloalkenyl, aryl, ($C_1$-$C_{10}$ alkyl)aryl; and
- $R^3$ is $C_1$-$C_4$ alkyl or $C_2$-$C_4$ alkenyl.

18. A compound having the formula

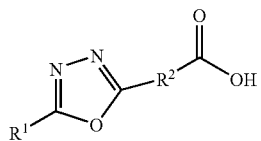

or a salt thereof, wherein
- $R^1$ is phenyl substituted with —OH;
- $R^1$ is optionally further substituted with one or more of $C_1$-$C_4$ alkyl or fluoroalkyl, $C_2$-$C_4$ alkenyl, $C_1$-$C_4$ alkoxy or fluoroalkoxy, —OH, —SH, phenyl, phenoxy, —$CO_2R^3$, or —$N(CH_3)_2$;
- $R^2$ is $C_4$-$C_8$ alkylene;
- $R^2$ is optionally substituted with one or more of $C_1$-$C_4$ alkyl or fluoroalkyl, $C_2$-$C_4$ alkenyl, $C_2$-$C_4$ alkoxy or fluoroalkoxy, halogens, —OH, —SH, phenyl, phenoxy, —$CO_2R^3$, —$N(CH_3)_2$, —$NO_2$, —$NH_2$, $C_3$-$C_{10}$ cycloalkyl, $C_3$-$C_{10}$ cycloalkenyl, aryl, ($C_1$-$C_{10}$ alkyl)aryl; and
- $R^3$ is $C_1$-$C_4$ alkyl or $C_2$-$C_4$ alkenyl.

* * * * *

UNITED STATES PATENT AND TRADEMARK OFFICE
CERTIFICATE OF CORRECTION

| | |
|---|---|
| PATENT NO. | : 7,417,061 B2 |
| APPLICATION NO. | : 11/440332 |
| DATED | : August 26, 2008 |
| INVENTOR(S) | : David Gschneidner |

It is certified that error appears in the above-identified patent and that said Letters Patent is hereby corrected as shown below:

Title Page, Item (73) Assignee:

Please remove "MHR Institutional Partners IIA LP, New York, NY"

and insert --Emisphere Technologies, Inc, Tarrytown, NY--

Signed and Sealed this

Ninth Day of June, 2009

JOHN DOLL
*Acting Director of the United States Patent and Trademark Office*